United States Patent [19]

Gumprecht

[11] Patent Number: 5,608,127

[45] Date of Patent: *Mar. 4, 1997

[54] HALOGEN EXCHANGE PROCESS FOR MANUFACTURE OF HYDROCHLOROFLUOROPROPANES

[75] Inventor: William H. Gumprecht, Wilmington, Del.

[73] Assignee: E. I. dupont de Nemours and Company, Wilmington, Del.

[*] Notice: The portion of the term of this patent subsequent to Jul. 25, 2006, has been disclaimed.

[21] Appl. No.: 809,152

[22] Filed: Dec. 16, 1991

Related U.S. Application Data

[63] Continuation of Ser. No. 477,737, Feb. 9, 1990, abandoned.

[51] Int. Cl.$^6$ .................................................. C07C 17/20
[52] U.S. Cl. ............................................................. 570/170
[58] Field of Search ............................................. 570/170

[56] References Cited

U.S. PATENT DOCUMENTS

| | | | |
|---|---|---|---|
| 1,978,840 | 10/1934 | Henne | 260/162 |
| 2,230,925 | 2/1941 | Benning | 260/653 |
| 2,431,969 | 12/1947 | Struve | 260/648 |
| 2,462,402 | 2/1949 | Joyce | 260/653 |
| 2,490,764 | 12/1949 | Benning et al. | 260/653 |
| 2,499,833 | 3/1950 | Perkins | 260/648 |
| 2,549,988 | 4/1951 | Perkins | 260/653 |
| 2,569,644 | 10/1951 | Stilmar | 260/653 |
| 3,201,483 | 8/1965 | Davis | 260/653.8 |
| 3,240,826 | 3/1966 | Davis | 570/170 |
| 3,287,424 | 11/1966 | Pacini et al. | 260/651 |
| 3,644,545 | 2/1972 | Buckmann | 260/653.7 |
| 4,078,007 | 3/1978 | Ferstandig | 260/653.7 |
| 4,129,603 | 12/1978 | Bell | 260/653.7 |
| 4,311,863 | 1/1982 | Gumprecht | 570/170 |
| 4,851,595 | 7/1989 | Gumprecht | 570/170 |

FOREIGN PATENT DOCUMENTS

| | | |
|---|---|---|
| 705927 | 3/1965 | Canada . |
| 0129863 | 1/1985 | European Pat. Off. . |
| 0300724 | 1/1989 | European Pat. Off. . |
| 0414370 | 2/1991 | European Pat. Off. . |
| 589167 | 6/1947 | United Kingdom . |
| 1585938 | 3/1981 | United Kingdom . |

OTHER PUBLICATIONS

Coffman et al., J. Am. Chem. Soc. 71, 979–980 (1949).
Hudlicky, "Chemistry of Organic Fluorine Compounds," Macmillan Co., NY (1962).
Sheppard et al., "Organic Fluorine Chemistry," W. A. Benjamin, Inc., NY (1969).
Paleta et al., Coll. Czech. Chem. Comm. 35, pp. 1867–1875 (1971).

*Primary Examiner*—Alan Siegel
*Attorney, Agent, or Firm*—Michael K. Boyer

[57] ABSTRACT

A process for the manufacture of a hydrochlorofluoropropane by halogen exchange using $SbF_{5-y}Cl_y$, where y=0 to 1, at 50°–100° C. to fluorinate a hydrochlorofluoropropane precursor characterized by the formula $C_3HCl_{7-x}F_x$, where x=2 to 5 and H is at a terminal carbon, wherein the degree of halogen exchange, p, and the number of moles, n, of $SbF_{5-y}Cl_y$ per mole of precursor is such that $(5-y)-(p/n)$ is at least 3. Such a process produces a more highly fluorinated hydrochlorofluoropropane substantially free of perhalogenated or carbon—carbon cleavage products.

16 Claims, No Drawings

HALOGEN EXCHANGE PROCESS FOR MANUFACTURE OF HYDROCHLOROFLUOROPROPANES

This is a continuation of application Ser. No. 07/477,737 filed Feb. 9, 1990, now abandoned.

BACKGROUND OF THE INVENTION

1. Field of the Invention

This invention relates to a halogen exchange process for the manufacture of hydrochlorofluoropropanes substantially free of the production of perhalogenated and carbon—carbon cleavage by-products. More specifically, but not by way of limitation, the present invention relates to the use of high-fluoride-content antimony pentahalides for the preparation of $CClF_2CF_2CHCl_2$ (HCFC-224ca), $CCl_2FCF_2CHClF$ (HCFC-224cb), $CF_3CF_2CHCl_2$ (HCFC-225ca), $CClF_2CF_2CHClF$ (HCFC-225cb) and $CF_3CF_2CHClF$ (HCFC-226ca) free of chloroform.

2. Description of Related Art Including Information Disclosed Under §§1,97–1.99

Hydrogen-containing fluorocarbons and chlorofluorocarbons (HFCs and HCFCs, respectively) are of current commercial interest as potential environmentally safe replacements for existing perhalogenated products which are now recognized as having high-ozone depletion potential. For example, the widely used solvent 1,1,2-trichloro-1,2,2-trifluoroethane (CFC-113, $CCl_2FCClF_2$) is suspected of contributing to the depletion of ozone in the earth's stratospheric layer. Recently, certain dichloropentafluoropropanes, $C_3HCl_2F_5$, such as $CF_3CF_2CHCl_2$ (HCFC-225ca), $CF_3CCl_2CHF_2$ (HCFC-225aa), and $CClF_2CF_2CHClF$ (HCFC-225cb) possessing properties similar to those of CFC-113, have been suggested as potential replacements for CFC-113. Because these $C_3HCl_2F_5$ compounds have a hydrogen substituent on a carbon atom adjacent to a halogen-substituted carbon atom, they can undergo dehydrohalogenation in the troposphere with little or none of these compounds surviving to reach the stratosphere.

Dichloropentafluoropropanes, $C_3HCl_2F_5$, notably $CF_3CF_2CHCl_2$ (HCFC-225ca) and $CClF_2CF_2CHClF$ (HCFC-225cb), have been prepared by the reaction of dichlorofluoromethane, $CHCl_2F$, with tetrafluoroethylene, $CF_2=CF_2$, in the presence of aluminum chloride [The Prins reaction: Joyce, U.S. Pat. No. 2,462,402; Coffman et al., J. Am. Chem. Soc. 71 979–980 (1949); Paleta et al., Coll. Czech. Chem. Comm. 35 1867–1875 (1971)]. This process suffers the disadvantage that extensive halogen exchange also takes place between the organic components and the aluminum chloride catalyst. One aspect of such an exchange is that substantial amounts of chloroform, $CHCl_3$, are produced from $CHCl_2F$. Chloroform is not only capable of entering into a competitive Prins reaction with $CF_2=CF_2$ (to produce a tetrafluoro derivative) but forms azeotropes with the pentafluoro products which prohibit subsequent purification thereof by simple distillation. The $CHCl_3$ contaminant is objectionable and must be removed. As a result, not only is the yield of the desired pentafluoro compounds lowered, but further costly processing is required to recover them substantially free of by-product $CHCl_3$.

In a recent U.S. Pat. No. 4,851,595, a process for preparing a hydrogen-containing fluoroethane, $CF_3CH_2F$, using a liquid-phase $SbF_{5-x}Cl_x$, where x=0 to 2, halogen exchange agent in a stoichiometric quantity sufficient to provide at least one fluoride for every chloride replaced in a chlorinated underfluorinated precursor under mild reaction conditions is disclosed. Since this reference deals exclusively with hydrochlorofluoroethanes, the above-mentioned problem associated with the $C_3HCl_2F_5$ azeotropes with $CHCl_3$ is not dealt with, but the reference does acknowledge that, depending primarily on the antimony pentahalide and reaction temperature employed, various by-products from side reactions involving carbon—carbon cleavage, chlorination and subsequent fluorine-for-chlorine radical exchange will be present.

Antimony pentafluoride ($SbF_5$) has also been employed as a halogen exchange agent in other processes. For example, Benning et al., U.S. Pat. No. 2,490,764, disclose its use for fluorinating compounds of the formula $ACF_2(CF_2)_nCF_2B$, where n is an integer of at least 1, A is H or Cl and B is Cl or F, to produce compounds of the formula $ACF_2(CF_2)_nCF_3$, where n is at least 1 and A is H, Cl or F. The highly fluorinated starting materials (propanes and higher) are extremely inert and require high temperatures (175°–350° C.) for their conversion to the more highly fluorinated derivatives. It appears, however, that side reactions leading to low-boiling by-products can occur under the rather stringent reaction conditions employed, notably with short-chain reactants. In Example III, designed to prepare a heptafluoropropane, $H(CF_2)_3F$ (b.p. –18° C.), by reaction of a chlorohexafluoropropane, $H(CF_2)_3Cl$ (b.p. 21° C.), with $SbF_5$ at 175° C. for 10 hours, the recovery of organic material, consisting of two main fractions, was only 70% by weight of the material charged. One of these fractions was $H(CF_2)_3F$, the other unreacted $H(CF_2)_3Cl$; relative amounts not disclosed. Unidentified lower-boiling fractions (–40° C. to –18° C.) were also obtained which strongly suggests that carbon—carbon cleavage to low-boiling $C_1$ and $C_2$ compounds and/or fluorination to perfluorinated $F(CF_2)_3F$ (b.p. –38° C.) had occurred in addition to the desired halogen exchange reaction.

The prior art recognizes such difficulties attending the use of $SbF_5$ as a fluorinating agent. Pacini et al., U.S. Pat. No. 3,287,424, teaches that $SbF_5$ produces very vigorous reactions, sometimes resulting in carbon—carbon cleavage, also that dehydrohalogenation can take place in which double bonds are created. Similarly, Davis, U.S. Pat. No. 3,201,483, discloses that attempts to fluorinate normally easily fluorinated organic compounds with $SbF_5$ usually result in highly exothermic reactions giving perfluorinated products.

Other related references are: Davis, U.S. Pat. No. 3,240,826 (1966), which utilizes $SbF_4Cl$, prepared by reaction of $SbF_5$ with $SbCl_5$, to replace Br with F in $CF_3CBr_3$, $CF_2BrCHBr_2$ and $CF_3CHBr_2$ at 35°–120° C.; and Davis, Canadian Patent 705,927 (1965), which employs $SbF_5$ mixed with sufficient bromine to maintain $SbF_5$ and salts thereof in liquid suspension for halogen exchange of fluorobromo compounds such as $CF_3CHBr_2$ and $CF_2BrCHBr_2$ at 20°–70° C.

SUMMARY OF THE INVENTION

The present invention provides a method of preparing at least one hydrochlorofluoropropane and typically a mixture of hydrochlorofluoropropanes having the general formula $C_3HCl_{7-x}F_x$, where x=3 to 6 and H is at a terminal carbon atom, by a halogen exchange reaction mechanism. According to the present invention, at least one precursor of the hydrochlorofluoropropane reaction product (again typically a mixture of precursors) having the general formula $C_3HCl_{7-x}F_x$, where x=2 to 5 and H is at a terminal carbon atom, is reacted with high-fluoride-content antimony pentahalides characterized by the formula $SbF_{5-y}Cl_y$, where y=0 to 1, under conditions that virtually eliminate the formation of perhalogenated and carbon—carbon cleavage compounds. By intentionally selecting, controlling and/or coordinating the initial number of moles (hereinafter referred to mathematically as "n") of $SbF_{5-y}Cl_y$ per mole of hydrochlorofluoropropane precursor along with the degree or number of halogen exchange stages to be effected (hereinafter referred to quantitatively as "p") such that (5–y)–(p/n) is at least 3 or greater, where y is the number of chlorides and (5–y) is the number of fluorides initially in the antimony pentahalide, the formation of the chlorinating agent, $SbF_3Cl_2$, is minimized. This in turn substantially eliminates the formation of perhalogenated by-products.

Thus, the present invention provides a process for manufacturing a hydrochlorofluoropropane comprising the steps of:

(a) contacting a hydrochlorofluoropropane precursor with $SbF_{5-y}Cl_y$, where y=0 to 1, at a temperature of from about 50° C. to about 100° C. for sufficient time to effect a degree of halogen exchange of p under conditions wherein the number of moles, n, of $SbF_{5-y}Cl_y$ per mole of said hydrochlorofluoropropane precursor is such that (5–y)–(p/n) is at least 3, thereby producing a hydrochlorofluoropropane free of perhalogenated or carbon—carbon cleavage by-products; and (b) recovering said hydrochlorofluoropropane.

It is an object of the present invention to provide a novel halogen exchange process for the preparation of hydrogen-containing chlorofluoropropanes represented by the formula $C_3HCl_{7-x}F_x$, where x=3 to 6, in high yields with minimal loss to perhalogenated by-products.

It is a further object of the present invention to provide such a process for preparing the hydrotrichlorotetrafluoro-, hydrodichloropentafluoro- and hydrochlorohexafluoropropanes which involves relatively mild operating conditions and does not require use of HF as fluorinating agent, thus avoiding HF-induced reactor corrosion and the need for high cost, high pressure equipment.

It is still a further object of the present invention to provide such a process for preparing hydrodichloropentafluoropropanes, including $CF_3CF_2CHCl_2$ (HCFC-225ca) and $CClF_2CF_2CHClF$ (HCFC-225cb), substantially free of chloroform, thereby enabling their recovery free of azeotropes with chloroform by simple distillation.

Fulfillment of these objects and the presence and fulfillment of other objects will be apparent upon complete reading of the specification and attached claims.

DESCRIPTION OF THE PREFERRED EMBODIMENTS

The halogen exchange process according to the present invention provides for the manufacture of hydrochlorofluoropropanes generally and in particular trichlorotetrafluoropropanes ($C_3HCl_3F_4$), dichloropentafluoropropanes ($C_3HCl_2F_5$) and chlorohexafluoropropanes ($C_3HClF_6$), where the hydrogen substituent is at a terminal carbon atom, in high yields and substantially uncontaminated by perhalogenated by-products starting from underfluorinated precursors. Also, any chloroform present in the precursor feed material is substantially destroyed during the halogen exchange process, so that the hydrochlorofluoropropane components present in the reaction product mixture can be recovered by simple distillation substantially free of $CHCl_3$ azeotropes.

For purposes of this invention, the use of the phrase "substantially free of perhalogenated and/or azeotrope-forming by-products" means that the content of such impurities in the product mixture is not observed or present in trace amounts only, preferably less than about 1 mole %.

The fact that the precursors can be smoothly, cleanly and substantially completely converted to the preferred tetra-, penta- and hexafluorinated propanes is surprising in view of the difficulties encountered in the other antimony pentahalide-based halogen exchange processes and the well documented difficulty of fluorinating —$CHCl_2$ groups adjacent to strongly deactivating —$CF_2$— and —$CF_2CF_3$ groups.

The hydrochlorofluoropropane precursor suitable for the fluoride exchange reaction according to the present invention can, in principle, be any hydrochloro- or hydrochlorofluoropropane possessing fewer fluorine radicals than the desired product. Typically this would include either essentially pure compounds or mixtures of compounds. Preferably the hydrochlorofluoropropane is characterized by the formula $C_3HCl_{7-x}F_x$, where x=2 to 5 and the hydrogen radical is located at a terminal carbon. It should be appreciated that since the desired product(s) of the fluoride exchange reaction according to the present invention are also characterized by the same general formula the products of the present reaction may also serve as the hydrochlorofluoropropane precursor reactant. Thus, for example, hydrotetrachlorotrifluoropropanes, such as $CF_3CCl_2CHCl_2$ (HCFC-223aa), $CClF_2CClFCHCl_2$ (HCFC-223ba) and $CCl_2FCF_2CHCl_2$ (HCFC-223ca), can be readily employed as precursors in the preparation of hydrotrichlorotetrafluoropropanes, such as $CF_3CCl_2CHClF$, (HCFC-224aa), $CF_3CClFCHCl_2$ (HCFC-224ba), $CClF_2CClFCHClF$ (HCFC-224bb), $CClF_2CF_2CHCl_2$ (HCFC-224ca) and $CCl_2FCF_2CHClF$ (HCFC-224cb) which can be reacted further to hydrodichloropentafluoropropanes. Compounds produced by this second stage or additional degree of fluoride exchange include $CF_3CCl_2CHF_2$ (HCFC-225aa), $CF_3CClFCHClF$ (HCFC-225ba), $CClF_2CClFCHF_2$ (HCFC-225bb), $CF_3CF_2CHCl2$ (HCFC-225ca), and $CClF_2CF_2CHClF$ (HCFC-225cb).

These $C_3HCl_2F_5$ compounds, singly or as mixtures, are candidates to replace CFC-113, normal b.p. approx. 47° C., as they have normal boiling points in the 50° to 56° C. range, are non-flammable, show sufficient stability in use in various industrial cleaning processes that utilize CFC-113 and have little ozone depletion potential. However, these compounds are also useful as intermediates (i.e., as hydrochlorofluoropropane precursors) to the formation of hydrochlorohexafluoropropanes, $C_3HClF_6$, such as $CF_3CF_2CHClF$ (HCFC-226ca) and $CClF2CF_2CHF_2$ (HCFC-226cb), again by way of the present halogen exchange reaction. These hexafluoro compounds have normal boiling points in the 20° to 22° C. range and are potentially useful as refrigerants and as intermediates to hydroheptofluoropropanes, also useful as refrigerants.

Underfluorinated precursor mixtures useful in the present halogen exchange reaction can be prepared by reaction of $CHCl_3$ (chloroform) or $CHCl_2F$ (HCFC-21) with the appropriate tetrahaloethylene, viz. $CF_2=CF_2$, $CF_2=CClF$ or $CF_2=CH_2$, in the presence of aluminum chloride, as disclosed by Joyce in U.S. Pat. No. 2,462,402, Coffman et al. in the Journal of the American Chemical Society 71, 979–980 (1949) and by Paleta et al. in Coll. Czech. Chem. Comm. 35, 1867–1875 (1971) or the like.

The preferred hydrochlorofluoropropane produced according to the halogen exchange reaction of the present invention is characterized by the formula $C_3HCl_{7-x}F_x$, where x=3 to 6 and the hydrogen radical is located at a terminal carbon. The most preferred products are $CF_3CF_2CHCl_2$ (HCFC-225ca) and $CClF_2CF_2CHClF$ (HCFC-225cb).

The halogen exchange process involves contacting a hdyrochlorofluoropropane precursor with an antimony pentahalide, $SbF_{5-y}Cl_y$, where y=0 to 1 (preferably $y \leq 0.75$, more preferably $y \leq 0.5$, and most preferably y=0). Preferably the antimony pentahalide is employed in the liquid phase. The actual contacting of the antimony pentahalide with the hydrochlorofluoropropane precursor can be accomplished by any of the methods as generally known in the art, and mixing can be facilitated by agitation, shaking and the like.

In the reaction that occurs, one or more chlorine radicals of the starting material (i.e., the underfluorinated precursor) are replaced (i.e., exchanged with) the fluoride of the antimony pentahalide, as illustrated in the following equations with $SbF_5$ as the halogen exchange agent:

$$C_3HCl_4F_3 + SbF_5 \rightarrow C_3HCl_3F_4 + SbF_4Cl \quad (1)$$

$$C_3HCl_3F_4 + SbF_5 \rightarrow C_3HCl_2F_5 + SbF_4Cl \quad (2)$$

$$C_3HCl_2F_5 + SbF_5 \rightarrow C_3HClF_6 + SbF_4Cl \quad (3)$$

$SbF_4Cl$ may also participate in the fluoride exchange process, as illustrated in the following equation:

$$C_3HCl_4F_3 + SbF_4Cl \rightarrow C_3HCl_3F_4 + SbF_3Cl_2 \quad (4)$$

It is preferred, however, to avoid or minimize involvement of $SbF_4Cl$ as halogen exchange agent for the present purpose since it leads to the formation of $SbF_3Cl_2$. This is undesirable because $SbF_3Cl_2$ and lower fluoride content antimony pentachlorofluorides have fluorinating potential that are too low for the present invention. Further, they show a definite tendency to produce perhalogenated by-products, particularly at the upper limit of the operating temperature range.

Thus, the $SbF_{5-y}Cl_y$ reactant according to the present invention includes $SbF_5$ and $SbF_4Cl$, defined by y=0 and 1, and mixtures thereof. It also includes related compositions defined by fractional values of y between 0 and 1 for which no simple structural formula can be drawn, but which can likewise be prepared by known processes, including the reaction of HF with $SbCl_5$, or reaction of $SbF_5$ with $SbCl_5$, or reaction of $SbCl_3$ with $F_2$ or reaction of $SbF_3$ with $F_2$ or $ClF$, in the stoichiometrically required proportions. Preferred are the low chloride-content compositions defined by y less than 1.0, more preferably y=0.5 or less, and most preferably y=zero, corresponding to $SbF_5$. Low chloride antimony pentahalides are preferred because Of their greater halogen exchange activities, and the superior results they provide.

The quantity of the antimony pentahalide employed may range widely and will depend on the particular organic precursor employed and its ease of fluorination via halogen exchange, the operating temperature and the result desired. Generally, there will be used at least about 0.5 mole, preferably at least about 1 mole, and, practically speaking, not more than about 5 moles of halogen exchange agent per mole of the precursor.

It is a feature of the present invention to control the reaction parameters so as to minimize the formation of $SbF_3Cl_2$ via the $SbF_4Cl$ exchange reaction (4) or the equivalent. By reducing or preventing the formation of $SbF_3Cl_2$ the subsequent production of perhalo by-products is minimized.

For purposes of this invention, the relationship $(5-y)-(p/n)$, where n is the initial number of moles of $SbF_{5-y}Cl_y$ per mole of hydrochlorofluoropropane precursor, $(5-y)$ is the initial number of fluorides in the antimony pentahalide, and p is the ultimate degree or number of halogen exchange stages, defines the number of fluorides expected in the residual or spent antimony pentahalide compound at the conclusion of the reaction. It is this particular mathematical expression or its equivalent which serves as the criterion for selecting, controlling, coordinating and/or manipulating the various reaction parameters such as to preclude or minimize the formation of $SbF_3Cl_2$.

In other words and as an alternative perspective, the mathematical expression $(5-y)-(p/n)$ can be viewed as a definition of the average degree of retention of fluorides in the antimony pentahalide exchange agent at any stage or time during the overall reaction, wherein the starting or initial number of fluorides per $SbF_{5-y}Cl_y$ is given by $(5-y)$ and at some subsequent time this initial value has diminished by $(p/n)$. In this alternate but equivalent interpretation, the p can be viewed as the average degree or number of fluoride exchanges that have occurred in the hydrochlorofluoropropane precursor (the average gain of fluorine radicals per precursor molecule), and the n is again the ratio of initial number of moles of exchange agent per mole of precursor. Thus, the term $(p/n)$ is effectively the average degree or number of fluorides lost per antimony pentahalide molecule. Consequently, the expression $(5-y)-(p/n)$ represents effectively the average number of fluorides remaining in the antimony pentahalide.

The greater the number of molar proportions of the antimony pentahalide, the smaller the value of y and the lower the temperature, the greater will be the fluoride content of the residual antimony pentahalide, and the smaller will be the amount of perhalo by-products produced. Thus, it is desirable to adjust the composition of the antimony pentahalide and its molar proportion such that the value of $(5-y)-(p/n)$ will be at least 3 at the end of each halogen exchange stage of the reaction, preferably at least 3.25, more preferably at least 3.5 and most preferably at least 4.0. Additional $SbF_5$ or other high-fluoride-content antimony pentachlorofluorides can be added to the reaction mixture, as needed, as the reaction proceeds. The number of halogen exchange stages, p (i.e., the number of precursor chlorine radicals to be replaced by the exchange agent fluorine radicals) can vary from 1 to 3 depending on the precursor and the desired fluorinated product. For example, the conversion of $C_3HCl_4F_3$ to $C_3HCl_3F_4$ involves one halogen exchange stage; its conversion to $C_3HCl_2F_5$ involves two stages; and its conversion to $C_3HClF_6$ involves three stages. The number of fluorides in the residual antimony pentahalide after p halogen exchange stages is given by $(5-y)-(p/n)$. When a single halogen exchange stage is effected, the number of fluorides in the residual antimony pentahalide is equal to $(5-y)-(1/n)$. When more than one halogen exchange stage is effected, e.g., 3 stages, the number of fluorides in the residual antimony pentahalide is given by $(5-y)-(p/n)$, where p in this instance is 3. In accordance with the invention, $(5-y)$ and n of the starting antimony pentahalide will be chosen such that $(5-y)-(p/n)$ will always be equal to or greater than 3 throughout the contacting step and at the end of the desired p number of stages to be effected. Stated another way, the minimum number of moles, n, of $SbF_{5-y}Cl_y$ per mole of precursor needed to result in a residual antimony pentachlorofluoride having 3 or more fluorides, z, after p halogen exchange stages, is given by the expression: n is greater than or equal to $p/[(5-y)-(z)]$.

It should be understood, as exemplified later, that p can be a fractional number as when a mixture of halogen exchange products is formed having different numbers of fluorine radicals. It should be further appreciated, particularly in view of the above description of the significance and interpretations of the mathematical expression $(5-y)-(p/n)$ relative to the critical numerical value 3 and the underlying intent to minimize formation of $SbF_3Cl_2$, that other equivalent mathematical expressions and critical numerical target values can be created and utilized consistent with the stated objective of minimizing in situ production of $SbF_3Cl_2$ Therefore, these alternate mathematical expressions should be considered equivalent to $(5-y)-(p/n) \geq 3$ for purposes of this invention.

Excess $SbF_5$, which is normally liquid, also provides for a fluid reaction mass, thereby promoting the halogen exchange reaction through good mixing of the reactants under agitation resulting in higher conversions of the organic component and fewer side-products. Fluid, more-easily-agitated reaction mixtures may also be provided by employing a liquid diluent inert to the reactants under the reaction conditions, such as perfluorocyclohexane, $F(CF_2)_7F$, and the like highly fluorinated alkanes disclosed in Benning U.S. Pat. No. 2,490,764.

It should be noted that HF is not needed as halogen exchange agent. However, if HF is present it will preferably be held to proportions less than one mole HF per mole of the antimony pentahalide; most preferably HF will be substantially absent since its presence increases the corrosivity of the reaction mass to ordinary materials of reactor system construction.

Reaction temperatures are normally in the about 50° to about 100° C. range, preferably will range from about 65° to about 85° C., most preferably about 70° to about 80° C. Temperatures below about 50° C. result in slower reactions. Temperatures in excess of about 100° C. can be used but are unnecessary, and may result in loss of reaction specificity.

The particular selection of pressure at which the exchange reaction is to take place is not critical. Atmospheric and autogenous pressures are most convenient and are therefore preferred.

The process according to the present invention may be conducted batchwise in a closed or ventable system. It may also be conducted in a continuous manner with the product(s) taken off intermittently or continuously. In addition, the process may be operated in a semi-continuous manner by reacting the organic precursor with a high-fluoride-content antimony chlorofluoride until the fluorinating power of the antimony chlorofluoride is reduced and thereafter treating the reduced fluoride content antimony chlorofluoride with HF to regenerate a high-fluoride-content antimony pentachlorofluoride by methods known in the art and recycling it to the process reactor. Since the $C_3HCl_2F_5$ isomers and the $C_3HClF_6$ isomers are all gaseous at temperatures above 50° C. at atmospheric pressure, it is convenient to maintain the reaction mixture at such temperature and bleed off a portion of the vapor phase intermittently or continuously through a pressure-control valve. This may be done while feeding the appropriate underfluorinated precursor to the reactor.

The volatile reaction product mixture exiting the reactor contains the hydrogen-containing product(s), unreacted starting material, if any, and by-products, if any. It can be treated by any of a variety of well-known techniques, including washing with aqueous caustic, then water and drying. A preferred isolation procedure involves scrubbing in aqueous HCl precooled to about −50° or −60° C. This facilitates collection of products as liquids. Since the precursors and the products derived therefrom boil sufficiently far apart, the scrubbed products can be further purified by fractional distillation. Unreacted or incompletely fluorinated material can then be recycled to the reactor.

The reaction vessel and its associated feed lines, effluent lines and ancillary equipment should be constructed of materials resistant to the action of the preferred reactants and products as well as any potential diluent or by-product including, by way of example but not limited thereto, the antimony pentahalide reactant, halocarbons, hydrogen fluoride, hydrogen chloride, and the corresponding halogens. Typical materials of construction, well known to the fluorination art, useful for this purpose include stainless steel, in particular of the austentitic type, and the well-known high nickel alloys such as "MONEL" nickel-copper alloys, "HASTELLOY" nickel-chromium alloys. Also suitable for reactor fabrication are such polymeric plastics as polyethylene, polypropylene, polychlorotrifluoroethylene, and polytetrafluoroethylene, generally used as linings.

The following examples are presented to further illustrate specific embodiments of the present invention compared to examples outside acceptable operating conditions. Each example utilized a stainless steel reactor consisting essentially of a 150 ml cylinder equipped with a polytetrafluoroethylene-coated magnetically actuated stirring bar. In each of the examples the reaction product stream was analyzed by means of gas chromatography. The gas chromatograph equipment included an HP-1 capillary column (crosslinked methyl silicone gum column of 50 m ×0.32 mm×1.05 μm film thickness, supplied by Hewlett-Packard, Avondale, Pa.) and a HP 5880 gas chromatograph equipped with a flame ionization detector. The response of the detector to each component was plotted versus time, with the area under each peak being proportional to its concentration in the gas stream. Gas chromatographic analyses are in area percent while all other percentages are expressed as weight percent except where indicated otherwise.

EXAMPLE 1

Antimony pentafluoride ($SbF_5$—47.1 grams, 0.219 mole) was poured into a 150 ml. stainless steel cylinder equipped with a polytetrafluoroethylene-coated magnetically actuatable stirring bar and contained in an argon-filled dry box. An appropriate valve was attached and, after pressure-testing the cylinder to 500 psig with dry $N_2$ gas, it was cooled in a solid $CO_2$-methanol mixture, vented and evacuated. HCFC-224ca ($CClF_2CF_2CHCl_2$—39.0 grams, 0.178 mole, 99.8% gas-chromatographic purity) was drawn into the cooled and evacuated cylinder from an inverted reservoir cylinder. The reactor was defrosted and placed in an oil bath preheated to 76° C. The reaction mixture was stirred and heated at 73°–75° C. for 4.5 hours. Volatiles were vented from the reaction vessel into 20.7% aqueous HCl cooled to about −50° C. while heating the reactor to 100° C. to drive over any unreacted HCFC-224ca, b.p. 91° C. The organic layer that formed was a colorless liquid weighing 31.2 grams. The reaction vessel contained 54.2 grams of a colorless solid (antimony pentachlorofluoride). The volatile and non-volatile fractions together amounted to 85.3 grams or 99.1% of the materials charged to the reactor.

Gas-chromatographic analysis of the organic fraction indicated the presence of the following components: $CF_3CF_2CHCl_2$ (HCFC-225ca)—47.9%, $CClF_2CF_2CHClF$ (HCFC-225cb)—1.19%, $CF_3CF_2CHClF$ (HCFC-226ca)—49.6% and unreacted $CClF_2CF_2CHCl_2$ (HCFC-224ca)—1.5%.

The above results indicate the halogen exchange reaction between $SbF_5$ and $CClF_2CF_2CHCl_2$ proceeded through about 1.5 exchange stages (i.e., p=1.5) and resulted in a residual antimony chlorofluoride having the approximate composition $SbF_{3.8}Cl_{1.2}$, as calculated by the expression (5−y)−p/n) =(5) −(1.5/1.23) =3.78, where (5−y) represents the number of fluorides in the starting antimony pentahalide, p is the number of halogen exchange stages, n is the $SbF_5$/HCFC-224ca mole ratio and 3.78 is the number of fluorides in the residual antimony pentachlorofluoride. The 3.78 calculated residual fluoride content of the antimony pentahalide is deemed reliable in view of the high (99.1%) material balance.

The above results also indicate that no perhalogenated or carbon-carbon cleavage by-products were formed under the reaction conditions employed.

EXAMPLE 2

The procedure of Example 1 was followed except that 65.9 grams (0.304 mole) of $SbF_5$ was preheated in the reactor to about 70° C., then 66.1 grams (0.301 mole) of HCFC-224ca, preheated to about 76° C., was injected into the reactor, and the mixture was maintained with stirring at 74°–76° C. for 2 hours. The volatiles were scrubbed into 20.7% aqueous HCl at about −50° C. while heating the reactor to 100° C. to drive off any unreacted HCFC-224ca.

There was thus obtained 52.8 grams of a colorless organic liquid, which was analyzed by gas chromatography and proton nuclear magnetic resonance spectroscopy ($^1$HNMR) with the following results:

| Compound (HCFC—) | G-C Area % | $^1$HNMR Mole % |
|---|---|---|
| $CF_3CF_2CHClF$ (226ca) | 22.4 | 21.4 |
| $CF_3CF_2CHCl_2$ (225ca) | 63.4 | 60.0 |
| $CClF_2CF_2CHClF$ (225cb) | 10.1 | 11.2 |
| $CF_3CCl_2CHF_2$ (225aa) | * | 4.0 |
| $CClF_2CF_2CHCl_2$ (224ca) | 4.0 | 3.5 |
| | 99.9 | 100.1 |

* Not detected by G-C as its peak lies underneath the larger HCFC-225ca G-C peak.

The results indicate the halogen exchange reaction proceeded through about 1.2 stages. Thus, it is calculated that the fluoride content of the residual antimony pentachlorofluoride was about 3.8, i.e. (5−y)−(p/n)=(5)−(1.2/1.01)=3.8.

Again, there was no indication that perhalogenated or carbon—carbon cleavage by-products were formed to any significant extent under the above reaction conditions.

EXAMPLE 3

This example illustrates the fluorination of mixed tetrachlorotrifluorohydropropanes and pentachlorodifluorohydropropanes to higher fluorinated hydrogen-containing chloropropanes. The mixture of tetrachloro- and pentachloro compounds, prepared by the $AlCl_3$-catalyzed reaction of $CHCl_2F$ with $CF_2\!=\!CCl_2$, had the following composition as determined by gas chromatography:

| Compound (HCFC—) | Area % |
|---|---|
| $CF_3CCl_2CHCl_2$ (223aa) | 15 |
| $CClF_2CClFCHCl_2$ (223ba) | 6 |
| $CClF_2CCl_2CHClF$ (223ab) | 3 |

| Compound (HCFC—) | Area % |
|---|---|
| $CCl_2FCF_2CHCl_2$ (223ca) | 71 |
| $CClF_2CCl_2CHCl_2$ (222aa) | 1* |
| $CCl_3CF_2CHCl_2$ (222ca) | 1* |
| $CHCl_3$ (HCC-20) | 1* |
| | 98 |

*The 222 series products evidently arise from $AlCl_3$-catalyzed disproportionation of $CHCl_2F$ during the reaction of $CHCl_2F$ with $CF_2\!=\!CCl_2$ followed by the reaction of $CHCl_3$ with $CF_2\!=\!CCl_2$.

The procedure of Example 2 was followed except that the feed reservoir (cylinder) for the organic component was padded with 100 psig of $N_2$ gas to aid in feeding this reactant (43.2 grams, 0.183 mole) into the reactor cylinder containing the $SbF_5$ reactant (75.1 grams, 0.346 mole). The feed cylinder was briefly post-heated to complete the organic feed. The reaction temperature was 74°–76° C. over 2 hours. The volatile fraction, collected after scrubbing in 20.7% aqueous HCl at −50° C., followed by three washings in ice water, weighed 26.2 grams. The solid residue in the reactor (antimony pentachlorofluoride) weighed 83.4 grams.

The organic reaction product was analyzed by gas chromatography and $^1$HNMR with the following results:

| Compound (HCFC—) | G-C Area % | $^1$HNMR Mole % |
|---|---|---|
| $CF_3CF_2CHClF$ (226ca) | 45.0 | 44.9 |
| $CF_3CF_2CHCl_2$ (225ca) | 18.9 | 17.7 |
| $CF_3CCl_2CHF_2$ (225aa) | 13.4 | 13.8 |
| $CClF_2CF_2CHClF$ (225cb) | 5.3 | 8.1 |
| $CF_3CClFCHCl_2$ (224ba) | 0.3 | not obs. |
| $CF_3CCl_2CHClF$ (224aa) | 1.1 | not obs. |
| $CClF_2CF_2CHCl_2$ (224ca) | 10.4 | 11.6 |
| $CCl_2FCF_2CHClF$ (224cb) | 0.2 | not obs. |
| $CF_3CCl_2CHCl_2$ (223aa) | 0.8 | 1.0 |
| $CClF_2CClFCHCl_2$ (223ba) | 0.4 | not obs. |
| $CClF_2CCl_2CHClF$ (223ab) | 0.3 | not obs. |
| $CCl_2FCF_2CHCl_2$ (223ca) | 3.5 | 3.0 |
| | 99.6 | 100.1 |

Presence of perhalogenated or carbon—carbon cleavage products was not observed. Nor was the presence of $CHCl_3$ which was undoubtedly fluorinated to the lower boiling $CHCl_2F$ and $CHClF_2$ during the reaction. The results indicate that the halogen exchange reaction proceeded through a maximum of about 2.5 stages (based on the formation of about 45 mole % of HCFC-226ca from the 223 series compounds via the 224 and 225 compounds). Thus, it can be estimated that the fluoride content of the residual antimony pentachlorofluoride was at least about 3.7 [i.e., (5−y)−(p/n)=(5)−(2.5/1.89)=3.7], which is well within the invention requirement that the fluoride content of the residual antimony pentachlorofluoride be at least 3 throughout the course of the reaction.

EXAMPLE 4

The general procedure of Example 1 was followed, except that a mixture of $SbF_5$ (83.5 grams, 0.385 mole) and $SbCl_5$ (170.2 grams, 0.569 mole) was employed. The mixture was heated with stirring at about 100° C. for 30 minutes to effect reaction between the two antimony compounds and produce $SbF_2Cl_3$ in situ. HCFC-224ca ($CClF_2CF_2CHCl_2$ —28.9 grams, 0.132 mole) was then added to the reactor. The reactor was closed, heated with stirring in an oil bath for 2 hours at 100°–103° C., removed from the bath and allowed to stand for 72 hours. Volatiles were vacuum-line transferred to a receiving cylinder which was vented to volatilize the organic material into 20.7% aqueous HCl at −50° C. The organic material, a yellow liquid, partially crystallized and smelled of chlorine. It was washed 4 times with ice-water. The second wash contained $Na_2SO_3$ to reduce the $Cl_2$ to chloride. Gas chromatographic analysis gave the following results:

| Compounds (HCFC—) | Area % |
|---|---|
| $CF_3CF_2CHCl_2$ (225ca) | trace |
| $CClF_2CF_2CHClF$ (225cb) | 0.07 |
| $CClF_2CF_2CCl_2F$ (215ca) | 0.11 |
| $CClF_2CF_2CHCl_2$ (224ca) | 99.63 |
| $CCl_2FCF_2CHCl_2$ (223ca) | 0.05 |
| Others | 0.03 |

The above is undesirable because $SbF_3Cl_2$ and lower fluoride content antimony pentachlorofluorides have fluorinating potential that are too low for the present invention. Further, they show a definite tendency to produce perhalogenated by-products, particularly at the upper limit of the operating temperature range.

EXAMPLE 5

The general procedure of Example 1 was followed except that a mixture of $SbF_5$ (39.1 grams, 0.18 mole) and $SbCl_5$ (36.3 grams, 0.12 mole) designed for form $SbF_3Cl_2$ in situ was heated with stirring in an oil bath to 100° C. over a 45-minute period. The reactor was then cooled in solid $CO_2$-methanol and evacuated, and $CClF_2CF_2CHCl_2$ (35.9 grams, 0.164 mole) was drawn into the evacuated reactor to provide an $SbF_3Cl_2/CClF_2CF_2CHCl_2$ mole ratio of 1.83/1. The reaction mixture was heated with stirring at 100°–102° C. for 2 hours, then vented into 20.7% aqueous HCl cooled to −50° C. while the reactor was being heated to 110° C. The resulting pale yellow organic layer was washed three times with ice water, the second wash containing $Na_2SO_3$ to destroy any $Cl_2$, to yield 24.6 grams of a nearly colorless liquid. The reactor residue weighed 81.4 grams. Thus, the recovery of materials amounted to 95.2% of that charged. Gas chromatographic analysis of the organic product gave the following results:

| Compounds (HCFC—) | Area % |
|---|---|
| $CClF_2CF_2CHClF$ (225cb) | 3.6 |
| $CF_3CF_2CHCl_2$ (225ca) | 0.3 |
| $CClF_2CF_2CHCl_2$ (224ca) | 95.9 |
| Others* | 0.2 |
|  | 100.0 |

*Includes $CF_3CClFCHCl_2$ (0.036), $CCl_2FCF_2CHClF$ (0.032), $CF_3CCl_2CHClF$ (0.028), $CClF_2CCl_2F$ (0.053), and $C_2Cl_2F_4$ (0.015) with the presence of $CClF_2CF_2CCl_2F$ and $CF_3CF_2CClF_2$ also observed.

Again the results show that $SbF_3Cl_2$, like $SbF_2Cl_3$ of Example 4, lacks the fluorinating potential needed to achieve practical results. They also indicate that this reagent tends to produce perhalogenated by-products. The fluoride content of the residual antimony pentachlorofluoride is calculated to be about 2.6, well below the required at least 3.0.

Having thus described and exemplified the invention with a certain degree of specificity, it should be appreciated that the following claims are not to be so limited but are to be afforded a scope commensurate with the wording of each element of the claims and equivalents thereof.

I claim:

1. A process for manufacturing a hydrochlorofluoropropane comprising the steps of:
   (a) contacting a hydrochlorofluoropropane precursor with $SbF_{5-y}Cl_y$, where y is less than 1, at a temperature of from about 50° C. to about 100° C. for sufficient time to effect a degree of halogen exchange of p under conditions wherein the number of moles, n, of $SbF_{5-y}Cl_y$ per mole of said hydrochlorofluoropropane precursor is such that (5−y)−(p/n) is at least 3.5, thereby producing a hydrochlorofluoropropane substantially free of perhalogenated or carbon—carbon cleavage products; and
   (b) recovering said hydrochlorofluoropropane.

2. A process of claim 1 wherein said hydrochlorofluoropropane precursor is characterized by the formula $C_3HCl_{7-x}F_x$, where x=2 to 5 and H is at a terminal carbon and wherein said hydrochlorofluoropropane produced is characterized by the formula $C_3HCl_{7-x}F_x$, where x=3 to 6 and H is at a terminal carbon.

3. A process of claim 1 wherein the temperature of the contacting step is from about 65° C. to about 85° C.

4. A process of claim 2 wherein the temperature of the contacting step is from about 65° C. to about 85° C.

5. A process of claim 1, 2, 3 or 4 wherein (5−y)−(p/n) is at least 4.00.

6. A process of claim 1, 2, 3 or 4 wherein y=0.

7. A process of claim 1 wherein y=0.

8. A process of claim 5 wherein y=0.

9. A process of claim 1 or 2 wherein said hydrochlorofluoropropane precursor is $CClF_2CF_2CHCl_2$ which is contacted with $SbF_5$ and wherein said hydrochlorofluoropropanes produced comprises at least one hydrochlorofluoropropane selected from the group consisting of $CF_3CF_2CHCl_2$, $CClF_2CF_2CHClF$ and $CF_3CF_2CHClF$.

10. A process for manufacturing a hydrochlorofluoropropane comprising the steps of:
   (a) contacting at least one hydrochlorofluoropropane precursor having a general formula of $C_3HCl_{7-x}F_x$, wherein x=2 to 5 and H is located at a terminal carbon atom, with $SbF_5$, under conditions which substantially eliminate formation of perhalogenated products; and
   (b) recovering a mixture containing at least one hydrochlorofluoropropane.

11. A process for manufacturing a hydrochlorofluoropropane comprising the steps of:
   (a) contacting at least one hydrochlorofluoropropane precursor with $SbF_5$ under conditions which substantially eliminate formation of perhalogenated products; and
   (b) recovering a mixture containing at least one hydrochlorofluoropropane having a general formula of $C_3HCl_{7-x}F_x$, wherein x=3 to 6 and H is located at a terminal carbon.

12. The process of claim 10 or 11 wherein said contacting is performed in the absence of hydrogen fluoride.

13. The process of claim 10 or 11 further comprising using the recovered hydrochlorofluoropropane as a hydrochlorofluoropropane precursor.

14. The process of claim 10 or 11 further comprising regenerating said antimony pentahalide with hydrogen fluoride.

15. The process of claim 10 or 11 wherein said antimony pentahalide is in a liquid phase and said liquid phase contains a diluent.

16. The process of claim 10 or 11 further comprising providing additional quantities of said antimony pentahalide during said contacting.

* * * * *